United States Patent
Hargus et al.

[11] Patent Number: 5,833,066
[45] Date of Patent: Nov. 10, 1998

[54] CARRYING CASE FOR ORAL AND NASAL INHALATION DEVICES WITH COUNTING MECHANISM

[75] Inventors: Susan D. Hargus; Karen J. Biehle, both of Marietta, Ga.

[73] Assignee: InhalerMate, LLC, Marietta, Ga.

[21] Appl. No.: 582,139

[22] Filed: Jan. 2, 1996

[51] Int. Cl.$^6$ .................................................. B65D 51/24
[52] U.S. Cl. ........................ 206/438; 116/317; 206/459.1
[58] Field of Search ................................. 40/312, 446, 459, 40/460, 484, 493, 495–498, 501, 503; 116/309–320; 206/459.1, 363.38, 438, 523, 570

[56] References Cited

U.S. PATENT DOCUMENTS

| | | | |
|---|---|---|---|
| 3,273,779 | 9/1966 | Mykleby | 206/523 |
| 3,638,603 | 2/1972 | Conover | 206/459.1 |
| 4,168,024 | 9/1979 | D'Alo | 206/570 |
| 4,573,580 | 3/1986 | Messer | 206/459.1 |
| 4,592,348 | 6/1986 | Waters et al. | 128/200.23 |
| 4,603,780 | 8/1986 | Duffy et al. | 206/523 |
| 4,782,966 | 11/1988 | Thackrey | 206/459.1 |
| 4,817,822 | 4/1989 | Rand et al. | 128/200.23 |
| 5,016,262 | 5/1991 | Cushing | 206/459.1 |
| 5,020,527 | 6/1991 | Dissertine | 128/200.23 |
| 5,111,918 | 5/1992 | Bako et al. | 190/121 |
| 5,117,952 | 6/1992 | Suh | 206/523 |
| 5,125,531 | 6/1992 | Wentz | 220/324 |
| 5,284,133 | 2/1994 | Burns et al. | 222/635 |
| 5,349,945 | 9/1994 | Clwass et al. | 128/200.23 |
| 5,363,842 | 11/1994 | Mishelevich et al. | 128/200.23 |
| 5,411,173 | 5/1995 | Weinstein | 222/162 |

*Primary Examiner*—Jimmy G. Foster
*Attorney, Agent, or Firm*—Thomas, Kayden, Horstemeyer & Risley, LLP; John A. Savio, III

[57] ABSTRACT

A unique carrying case for oral inhalers, nasal inhalers, other medications, or similar items that protects such devices from damage while providing a counting mechanism for the user to track the number of doses dispensed from an inhaler, other medication, or similar item. The preferred embodiment described in the drawings includes a case constructed of lightweight, impact-resistant, molded plastic that is opened and closed by a hinged lid. The counting mechanism shown in the preferred embodiment depicts a three-digit, manual, mechanical device with digits from zero to 999. The user operates each digit independently by pressing a "+" button to advance or a "−" button to retract the digits. A polyurethane foam pad surrounds the counting mechanism. The foam protects the counting mechanism and inhaler from damage and reduces noise that may result when an inhaler is allowed to move freely within the case. The case may be carried in a pocket, purse, or bag or may be carried with an optional wrist strap or clip. The carrying case protects inhalers from dirt, water, sunlight, or damage and provides adequate space for a pharmacist to affix a prescription label. The counting mechanism allows a user to track the number of doses administered from an inhaler after each dose of medication is delivered. This serves as an important reminder to refill the inhaler prescription before the inhaler canister is empty and provides the user with a method to avoid unknowing use of an empty canister.

12 Claims, 3 Drawing Sheets

CARRYING CASE FOR ORAL AND NASAL INHALATION DEVICES WITH COUNTING MECHANISM

FIELD OF THE INVENTION

This invention relates to a carrying case for medication dispenser devices, more specifically, the present invention relates to a carrying case with a counting mechanism permanently attached to the lid of the case.

BACKGROUND OF THE INVENTION

Inhalation devices are well-known alternatives to parenteral administration of medication and are available in a variety of inhaler styles. Methods of administration for inhaled medications include metered-dose inhalers, nasal spray devices, and nebulizers. These medications provide a rapid onset of action and relief of symptoms by applying medication directly to the lung tissue or nasal mucosa.

Inhalers are an essential component in the management of asthma, allergic rhinitis and other common medical ailments. More recent uses include pain management, diabetes insipidus, and osteoporosis.

Oral metered-dose inhalers, which administer medication directly to the lung tissue, consist of a pressurized metal canister filled with medication. The aerosol canister is inserted into a hollow plastic outer-body with an opening on one end that becomes a mouthpiece for drug administration. The patient administers a dose by pressing down on the metal canister and activating the device.

Nasal inhalers have two basic designs. The first design, a nasal metered-dose inhaler, is similar to the oral metered-dose inhalers with a pressurized aerosol canister placed inside a plastic outer body. The second design, a nasal spray, consists of a glass or plastic container fitted with a pump-style administration device. The patient pushes the bottom of the container to administer the dose.

The third type of administration device, a nebulizer, uses a machine to provide a fine mist of drug to the patient. The active drug is mixed with saline or other diluent and is administered through tubing connected to the nebulizer.

The number of inhaler users in the United States is large and growing. According to statistics from the National Health Interview Survey, 88,226,000 people reported chronic respiratory or sinus conditions in 1992. These conditions are often treated with inhaler-type medications. The growth in the number of allergy and asthma sufferers is expected to continue. Death rates of asthma patients in the United States increased from 0.8 per 100,000 general population in 1977 to 2.0 per 100,000 in 1991. Estimated total hospital and drug store sales on beta-adrenergic[1] metered-dose inhalers increased from 10.3 puffs per person in 1976 to 31.0 in 1991; those for inhaled corticosteroids[2] from 0.44 puffs per person in 1976 to 5.44 in 1991. Sales of administration-related devices have also increased.[3]

[1] Medications that dilate airways used to reverse bronchospasm characteristic of acute asthma attacks.
[2] Medications used to reverse the inflammatory response characteristic of asthma and allergy attacks.
[3] Sly, R. Michael "Changing asthma mortality and sales of inhaled bronchodilators and anti-asthmatic drugs" *Annals of Allergy*, Vol. 73, November 1994 p. 439–443.

Patient compliance, motivation, and understanding of these diseases and treatments are essential factors for successful control of asthma and allergic rhinitis. Patients must administer their medications at the proper schedule and dosage without direct supervision of doctors or other health care personnel. Patients who follow their regimens correctly can control symptoms and reduce asthma and allergy relapses, as well as trips to the physician's office or hospital. Studies evaluating new asthma medications indicate that patients often under-use, over-use and/or inappropriately use their medications. A study of patients utilizing peak flow meters and inhalers found only 40% of patients comply with treatment regimens, despite extensive educational programs and follow-ups.[4] Because of the consequences of non-compliance, new products to improve patient compliance and utilization are well-received by patients and health care providers alike.

[4] Chmelik, Frank and Doughty, Andrea "Objective measurements of compliance in asthma treatment" *Annals of Allergy*, Vol. 73, November 1994 p. 527–532.

Today's metered-dose inhalers do not have a way to track the number of doses released from the canister and cannot compute the number of doses remaining in the canister. Once the inhaler is dispensed from the pharmacy, the user is responsible for remembering the number of doses remaining in the container. Various methods to determine the number of doses remaining in the container have been utilized over the years. Some users drop the metal canister into a glass of water; the container sinks when it contains medication or floats when almost empty. Other users shake the container to listen for medication in the canister; still others utilize a paper calendar or table and cross-off the number of doses as they are administered.

These methods are inaccurate so users often find themselves with an empty inhaler canister. Asthma patients who unexpectedly find themselves without medication during times of stress or acute asthma attacks often experience serious medical complications and even death. Allergic rhinitis patients must take regular doses of corticosteroids to avoid severe allergy symptoms that occur if therapy is stopped abruptly. Because oral and nasal inhalers are prescription drugs that require a physician's authorization for refills, emergency refills are difficult to obtain when the patient is away from home or uses a mail-order pharmacy or when the patient's regular pharmacy is closed. Because the inhaler often does not have a prescription label affixed to the inhaler body, the patient may be unaware that the prescription has no more refills remaining. When the inhaler prescription can no longer be refilled, the pharmacist must contact the physician for authorization of additional refills, which inconveniences the patient, pharmacist and physician. When symptoms are severe or the physician is unavailable, the patient must seek medical attention from a hospital or clinic.

If patients were aware of the number of doses they have used and the approximate number remaining in the canister, they could anticipate refills early so the complications, inconveniences and added costs of an untreated asthma attack or allergic reaction can be avoided. A counting mechanism designed to track the number of doses administered from the inhaler will provide a way to monitor usage and avoid running out of medication.

Several prior art counting and timing devices have been developed and patented. Examples include the following:

U.S. Pat. No. 5,020,527, issued Jun. 4, 1991 to Pauline L. Dessertine, in which a counting mechanism and timing device is attached to the main body of the inhaler. The counting mechanism is advanced by actuation of the inhaler; the timer tracks time between inhalations. Two windows on the inhaler body display the information for the user.

U.S. Pat. No. 5,284,133, issued Feb. 8, 1994 to James S. Burns and Daniel R. Marshak, in which a controller, timer, actuator and signaling device is utilized to monitor patient compliance.

U.S. Pat. No. 5,349,945, issued Sep. 27, 1994 to Anthony Clwass and Brian R. Law, in which an indicator device marks progression of the canister from "full" to "empty". The user views the display through a window located in the hollow plastic body of the inhaler. The indicator is advanced by actuating the canister.

U.S. Pat. No. 5,363,842, issued Nov. 15, 1994 to David J. Mishelevich, Ted W. Lanpher, Gregory B. Lanpher, and James Long, in which a device gives feedback to the patient regarding correct and consistent usage of the inhaler. The device records the flow, volume, time and date of each dose for review by healthcare professionals. The device is incorporated into a hollow plastic boot.

U.S. Pat. No. 5,411,173, issued May 2, 1995 to Albert Weinstein, in which a counting mechanism attachment is clipped onto the side wall of the plastic inhaler body. The counting mechanism advances with actuation of the inhaler. A window on the body of the inhaler displays doses dispensed.

U.S. Pat. No. 4,592,348, issued Jun. 3, 1986 to William C. Waters and Charles I Wilmer, in which a device assists in proper timing of the release of the aerosol medication with the user's inhalation.

U.S. Pat. No. 4,817,822, issued Apr. 4, 1989 to Paul K. Rand, Carole A. Osterwell, and Robert E. Newell, in which a "cap" is placed on top of the aerosol canister. Actuation of the inhaler advances the counting mechanism. The cap holds the canister by use of a retaining ring and is not removed from the inhaler body. A window indicates "full", "¾", "½", "¼" and "empty".

Each of these prior art counting mechanisms depends on activation of the inhaler to advance the counting mechanism and provides "automatic" counting. Designs incorporating the counting mechanisms into the plastic outer body of the inhaler add substantial cost to the inhaler. These designs also require customization of the counting mechanism for each specific brand and design of inhaler. The more complex devices would be extremely costly and require training for the patient and health care professional to use the inhaler correctly. One device requires programming by a pharmacist or physician; data collected by the device is stored until the physician or pharmacist interprets the information. The patient does not have access to information collected by the device until the next office visit or prescription refill.

Another difficulty with inhaler use is design of the inhaler canister and containers. Inhalers are expensive and important items that must be protected from dirt, dust, water, sunlight, and damage. One inhaler may be carried for weeks or months until it is replaced. However, allergy and asthma attacks can happen at any time, so inhalers made of plastic, metal or glass are frequently carried unprotected in purses, pockets, book bags, briefcases, or such items for immediate use. Consequently, they may become separated, broken, clogged or accidentally activated. Another difficulty is that although inhalers provide easy access to the patient, they are not particularly child-resistant. A small child can easily press on the container and spray active drug into his or her eyes, nose or mouth, in addition to wasting expensive medication. None of the prior art devices address the issue of protection of the inhaler from the above hazards.

Finally, prescription labels are difficult to place on inhaler canisters and containers. The container shapes are irregular and small in size. The labels are often too large for the canister or container so the pharmacist usually places the label on the outer cardboard shipping box. The box is usually discarded by the patient so vital labeling information necessary for prescription refills, school use and emergency situations is lost.

Currently, a carrying case designed specifically for oral and nasal inhalers is not available. A case with a counting mechanism would be very helpful to the user. Since prior art devices focus on the plastic outer body of the inhaler, each type of inhaler must be redesigned to accommodate the counting mechanism. If the user breaks, soils or loses the inhaler outer body, another expensive plastic outer body must be purchased. At present, none of the prior art devices have found their way into mainstream inhaler usage, possibly because of manufacturing difficulties in accommodating different inhaler devices and the unacceptable increase in cost of the device in an increasingly cost-conscious health care environment.

SUMMARY OF THE INVENTION

Briefly described, the present invention comprises a carrying case for a fluid medication dispenser. Typically, the medication dispenser comprises an oral or nasal inhaler, such as those used by asthmatics. The carrying case preferably comprises a main or lower portion forming a cavity for receiving the medication dispenser. This main or lower part of the carrying case defines a cavity and is typically constructed of rectangular sidewalls connected to a pair of end walls and a bottom wall. The rectangular sidewalls are preferably constructed to be outwardly convex to give greater strength to the carrying case.

The carrying case also comprises a cover or lid mounted by a hinge to the main or lower portion. This lid should preferably be sized such that the lid has a lower margin that will fit with a top opening of the main or lower portion. In this way, the cover or upper part may be rotated about the hinge and rest upon the main or lower part forming a closed volume. The medication dispenser will thus be entirely contained within the carrying case. A hasp or other common latching mechanism preferably is attached to the exterior of the main or lower part for securing the lid to the lower portion. This latch or hasp may comprise any group of devices to connect to the upper and lower part securely, but releasably.

Finally, a counting mechanism is embedded inside the lid. This will prevent damage to the counter from moisture or dirt, for example. The counting mechanism may be attached by attachment methods in common use. While the particular type of counting mechanism used is not critical to the present invention, the preferred embodiment discloses a three digit counting mechanism actuated by buttons.

In an improvement to the present invention, the counting mechanism may be surrounded by a polyurethane foam material. This polyurethane foam material should surround and encase the counting mechanism to prevent the counting mechanism from being damaged. This foam material provides the further advantage of preventing damage to the medical dispenser.

In another improvement to the present invention, an O-ring may be seated around the top opening of the main part of the case such that when the lid rests upon the main part, and the hasp is fastened, the case will be water tight. Although the construction of the O-ring is not critical to the present invention, the preferred embodiment discloses a rubber O-ring.

The carrying case may be constructed of any known material. However, it is preferable that the material out of which the carrying case is constructed is light weight and rigid. An excellent material for use in constructing the carrying case is a molded plastic material.

In a further improvement of the present invention, a molded plastic eyelet may be attached securely to the top of the cover or lid of the case. In this way, a common securing means may be attached to the eyelet and then the securing means attached around a user's wrist or neck. In another aspect, the main part of the carrying case could have an upper rim which is sloped with respect to the bottom wall of the case. The cover or lid should be correspondingly sloped. In this improvement to the preferred embodiment, a user would have easier access to the medical dispenser.

An advantage of the present invention is that the present invention is designed to accommodate most styles and brands of oral and nasal inhalers.

Another advantage of the present invention is that it does not require complex and costly changes to existing inhaler devices. Inhaler replacement costs will not foreseeably be affected by this invention.

Another advantage of the present invention is that it does not require manufacturers to redesign their product.

Another advantage of the present invention is that it will not be affected by changes in design of the inhaler canister or containers, because the size of the carrying case may be easily altered to accommodate new classes of inhalers.

Another advantage of the present invention is that it does not depend on actuation of the inhaler to advance the counting mechanism.

Another advantage of the present invention is that it protects the inhaler from dirt, water, sunlight and damage.

Another advantage of the present invention is that it protects the inhaler from accidental actuation caused when the inhaler impacts with other items in the user's purse, bag, briefcase, pocket, or other location.

Another advantage of the present invention is that it stores inhalers that must be kept cold in a refrigerator or cooler while traveling.

Yet another advantage of the present invention is that with the use of a wrist strap or clip with the present invention allows the user to easily carry the inhaler while jogging, exercising or during other activities. The counting mechanism of the present invention also allows the user to keep count of doses administered. For example, the patient advances the mechanism one count for each puff administered. Because physicians, pharmacists and patients can monitor the number of doses dispensed by the patient, the counting mechanism aids in patient compliance.

Another advantage of the present invention is that this invention allows the user to decide when to refill the inhaler based on the number of inhalations dispensed from the container. This is the most important function of the counting mechanism. Fox example, an inhaler that is designed to deliver 200 doses should be refilled after 150 doses are dispensed. The user may continue to use the old inhaler until the full 200 doses have been dispensed—however, the patient has a new canister available for use once the old canister is empty. This is especially important to the corticosteroid user whose inhaler may be out of medication but still performs as if it contains medicine. Because this medication does not provide immediate relief from symptoms, the patient may experience hours or days of severe symptoms once doses are missed because of ineffective dosing by an empty inhaler. The present invention will reduce the number of emergency refills and medical problems arising from an unexpectedly empty inhaler. Patients utilizing more than one type of inhaler can track the need for refills by using a separate case for each inhaler.

Compliance and cost savings are two important issues in patient care. The counting mechanism optimizes inhaler use by reminding the user to refill at the proper time and keeping a tally of doses administered. This will save time and money for all persons involved in care of the patient. The present invention is simple to use, inexpensive, re-usable and requires very little patient training and education. The size and shape of the carrying case provides a place to affix a prescription label, which is a valuable source of information for users and health care professionals. Further objects and advantages of the invention will become apparent from a consideration of the drawings and ensuing description.

BRIEF DESCRIPTION OF DRAWINGS

FIGS. 11, 11A and 11B are enlarged top, side and end views of a three-digit mechanical counting mechanism.

DETAILED DESCRIPTION OF THE PREFERRED EMBODIMENT

Figure 1:
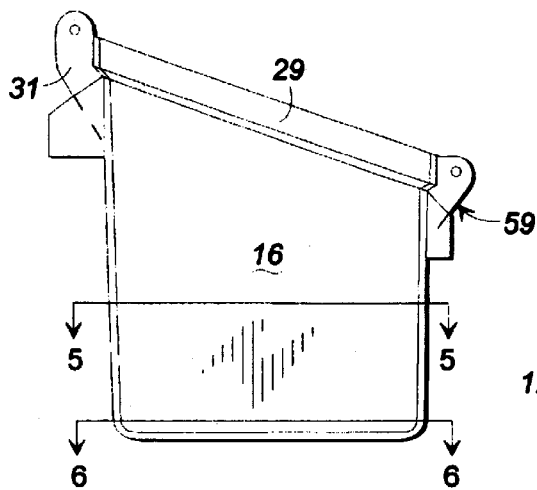
FIG. 1 is a side view of lower section of carrying case.
Figure 1A:
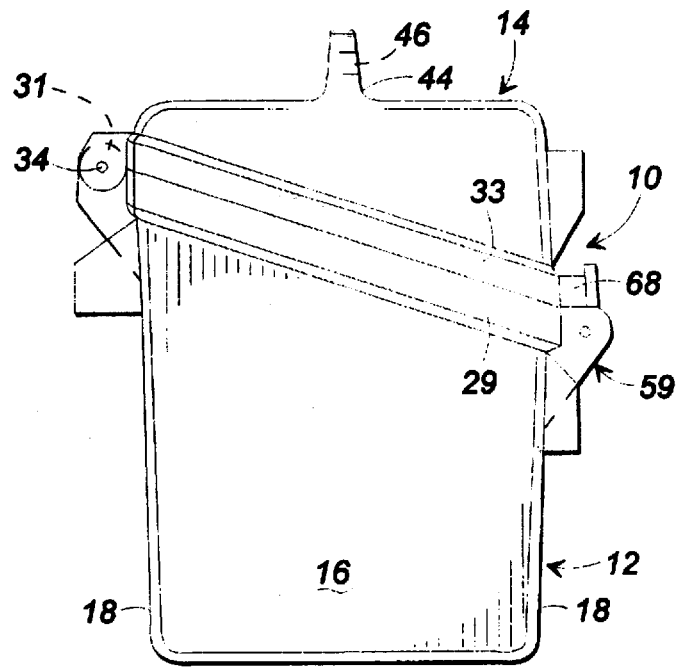
FIGS. 1A, 1B & 1C are side, end, and top views of carrying case when lid is closed.
Figure 1B:
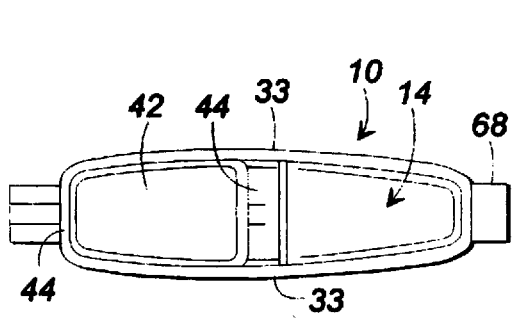
Figure 1C:
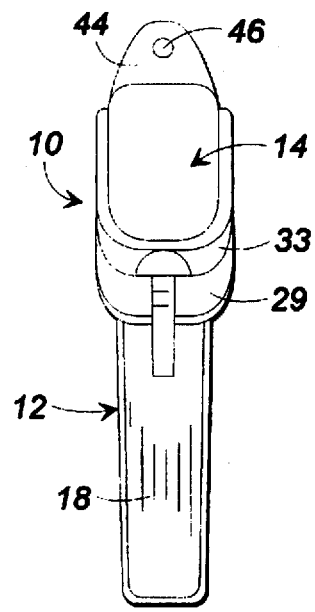

The preferred embodiment of the carrying case included in the present invention depicts U.S. Pat. No. 5,125,531 "Carrying Case for Personal Articles," issued Jun. 30, 1992 to Richard J. Wentz, as manufactured by Witz, Inc. A distributor relationship has been granted by Witz, Inc. for use of this carrying case in the present invention. The present patent application does not encompass the Witz design, but merely portrays it as an example. A detailed description of the case is as follows:

The case which is the preferred embodiment of the present invention is broadly denoted by the numeral 10 and is shown in FIGS. 1A, 1B, and 1C. Case 10 has a lower, main part 12 which is hollow and has an open upper end. Lower part 12 is, in essence, a housing for containing personal articles, including oral inhalers, nasal inhalers and other related products. The lower part 12 is attached to a cover (upper part 14) and is hinge-mounted to allow opening and closure of the case. This allows access to the inhaler housed in lower part 12.

Figure 2:
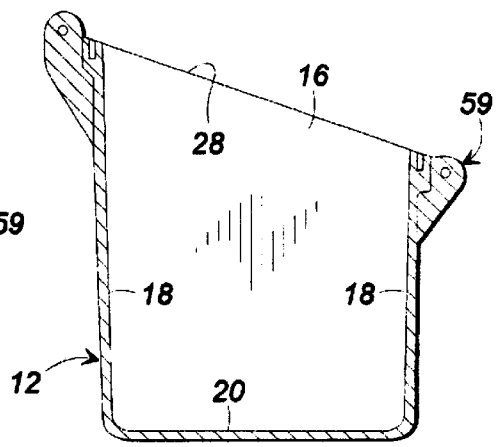
FIG. 2 is a vertical section through lower part of FIG. 1.
Figure 3:
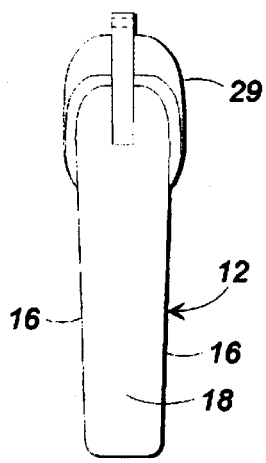
FIG. 3 is an elevated view of lower section of carrying case.

Lower part 12 includes a pair of opposed sidewalls 16, a pair of opposed end walls 18 and a bottom wall 20 (FIG.2). Walls 16, 18 and 20, are integral with each other and typically are formed in a molding process using suitable plastic, which is generally light-weight and impact-resistant.

Figure 5:
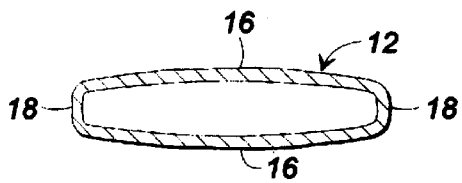
FIGS. 5 and 6 are cross-sectional views of line 5—5 and 6—6 shown on FIG. 1.
Figure 6:
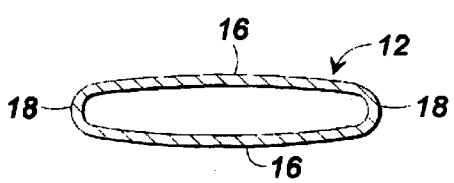

Sides 16 (FIGS. 5 and 6) has convex outer surfaces, which reinforce the side walls, increase bending strength and provide additional space for the inhaler.

The upper margin of lower part 12, being inclined with respect to bottom wall 20 as shown in FIG. 2 also provides additional space for the inhaler and helps keep the inhaler in the lower part of the case in the event that the case tips over when the lid is open.

Reinforcement strips or bands placed on the outside of the case (29 extends around lower case part 12 and 33 extends around the cover 14). This feature permits the sidewalls to be relatively thin yet strong (FIG. 1A).

Figure 8:
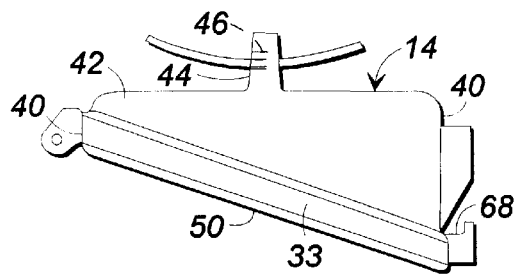
FIG. 8 is a side view of the lid.

Cover 14 includes a pair of opposed sidewalls 38, a pair of opposed end walls 40 and a top wall 42 (FIG. 8). They are composed of the same material described in lower part 12. Cover 14 has an eyelet 44 with a hole 46 for receiving a cord, string or clip for use when carrying the case (FIG. 8).

Figure 4:
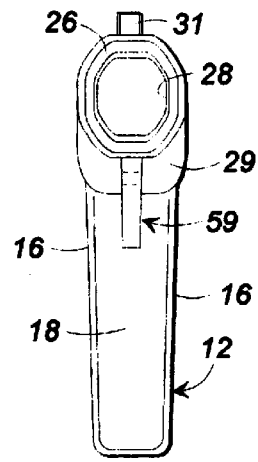
FIG. 4 is a similar view of FIG. 3, but showing the opposite end of lower section of carrying case.
Figure 7:
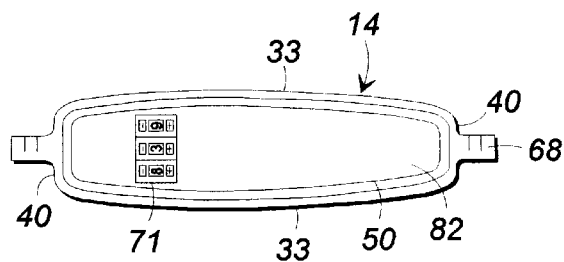
FIG. 7 is a bottom view of lid when carrying case is open. The mechanical counting mechanism, encased in polyurethane foam, is displayed.

Rib 50 (FIG. 7) is located on the lower margin of cover 14 and is adapted to engage the O-ring 26 (FIG. 4) located on lower part 12 of the case. Rib 50 prevents water from seeping into the case when the case is closed. The O-ring 26 acts as a seal, rendering the case watertight when the cover is on the lower part of the case and the case is closed. The O-ring 26 surrounds the top opening 28 (FIG. 4) of lower part 12.

Figure 9:
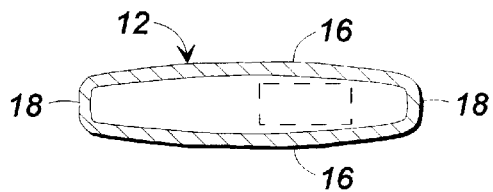
FIG. 9 is a similar view of FIG. 5, depicting an inhaler placed into the lower section of carrying case. The inhaler is depicted by dashed lines.
Figure 10:
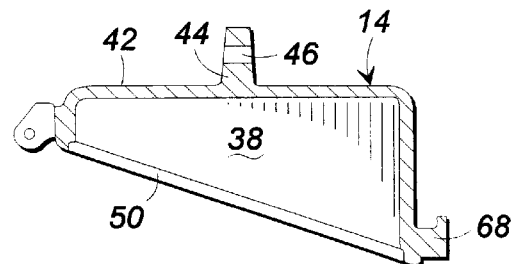
FIG. 10 is a vertical section through lid.

FIG. 9 depicts an inhaler housed in lower part 12.

Once the case is closed, any suitable, releasable, locking mechanism can be used to lock and unlock the cover to the lower part. The preferred embodiment portrays a conventional hasp 59 (FIG. 1A).

Thus the case, when closed, can carry inhalers of different types in a watertight housing and can be carried in a pocket or bag or by use of a wrist strap or clip. The area inside cover 14 is also used to house the mechanical counting mechanism, which is an integral part of the present invention.

Figure 11:
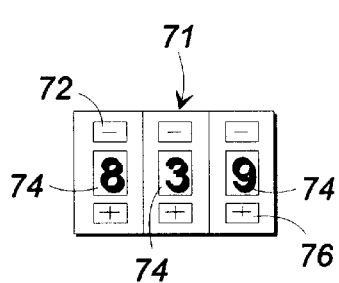
Figure 12:
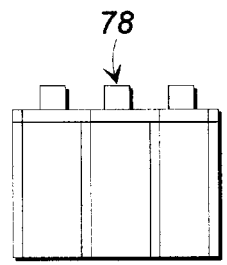
Figure 13:
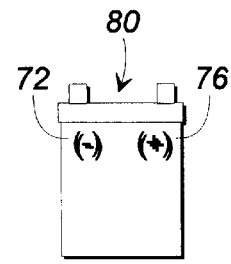

The preferred embodiment includes counting mechanism 71 (FIG. 7), such as the switch assembly AC 2Y139 distributed by IVO Industries, USA. Counting mechanism 71 consists of three independently operated switch assemblies. The switch assemblies are joined together to form the counting mechanism 71. The counting mechanism 71 is further depicted by length 78 and width 80 of the switch assemblies (FIG. 11A and 11B). Each switch is operated independently, allowing for a total count of 999 when all digits are utilized. The numbered wheels 74 may be advanced forward by pressing button 76 or backward by pressing button 72 (FIG. 11B). A positive button 76 (labeled with a "+") advances the numbered wheel forward one digit when pressed. A negative button 72 labeled with a "–") retracts the numbered wheel backward one digit when pressed (button 72). Each numbered wheel displays the digits zero through nine (numbered wheels 74). Therefore, in order to advance the counting mechanism 71 from "9" to "10," the user advances the middle digit to "1" and the right digit from "9" to "0" (the display reads "0-1-0"). The counting mechanism 71 may be reset to zero by simply advancing either buttons 72 or 76 until zeros appear in the display (numbered wheels 74). The present patent application does not encompass this specific counting mechanism, but merely portrays the device as an example. The counting mechanism 71 is surrounded by polyurethane foam 82 (FIG. 7), which protects the counting mechanism, as well as protecting the inhaler from damage and reducing noise that results if the inhaler is allowed to move freely within the case.

List of Reference Numerals

10. Denotes entire carrying case.
12. Main or lower part of case in which the inhaler is placed.
14. Cover or upper part of case in which the counting mechanism is placed.
16. Side walls of lower part of case.
18. Opposed end walls of lower part of case.
20. Bottom wall of lower part of case.
26. O-ring or seal.
28. Top opening of lower part 12.
29. Reinforcement strip or band on lower part of case.
33. Reinforcement strip or band on cover.
38. Opposed side walls for cover 14.
40. Opposed end walls for cover 14.
42. Top wall for cover 14.
44. Eyelet for receiving cord, wrist strap or clip.
46. Hole for cord, string or buckle.
50. Rib for O-ring 26 to prevent water seepage.
59. Conventional hasp or locking mechanism.
68. Projection on cover for hasp.
71. Front (top) view of counting mechanism when affixed to lid of carrying case.
72. Button on counting mechanism that reduces total count by one digit (–).
74. Numerals on wheel of switch assembly that display the count.
76. Button on counting mechanism that increases total count by one digit (+).
78. Enlarged side view of length of counting mechanism depicting 3 switch assemblies.
80. Enlarged side view of width of one switch assembly depicting "+" and "–" buttons.
82. Polyurethane foam pad to protect counting mechanism.

Operation of the carrying case and counting mechanism

To operate the present invention depicted in FIG. 1, the user opens the lid of the carrying case when a dose of medication is needed. The case is opened and closed by use of a hinged lid. The user removes then inhaler from the carrying case and then administers a dose of the inhaled medication in a manner prescribed by the physician. After the dose has been administered, the user presses the (+) button on the mechanical counting mechanism to advance the digits displayed the appropriate number of times that corresponds to the number of sprays administered. The type of mechanical counting mechanism depicted in the preferred embodiment consists of a spring-loaded device that moves one of three numbered wheels each time a button is pressed—one wheel for each digit. Each digit of the counting mechanism may be actuated by using one of two buttons: a positive button (labeled with a "+") that advances a numbered wheel forward one digit when pressed and a negative button (labeled with a "–") that retracts the numbered wheel backward one digit when pressed. Each wheel displays the digits 0–9. Therefore, in order to advance the counter from "9" to "10", the user advances the middle digit to "1" and the right digit from "9" to "0"(the counter reads 0-1-0). After advancing the counting mechanism, the user returns the inhaler to the carrying case and closes the hasp into the locking position. Closure of the case creates a water-resistant seal. A polyurethane foam pad placed on the inside of the lid provides protection for the counting mechanism by reducing rattling and also reduces noise that occurs when an inhaler moves freely within the case. The carrying case may be freely carried in a pocket or purse or by use of an optional wrist strap or a clip that may be snapped onto a belt loop, gym bag or other item.

The present invention resolves several issues faced by users of oral and nasal inhalers. The carrying case of the present invention provides many improvements over the prior art:

For example, a manner of protecting any of a group of inhalers, other medications or similar items from dirt, water, sunlight, damage and accidental activation is provided.

A method of keeping a count or tally of the number of doses dispensed from the inhaler to remind the user to refill the inhaler before the canister is depleted of medication is also provided by the preferred embodiment. This prevents users from unknowingly using an empty inhaler.

The preferred embodiment also discloses a manner of storing and carrying inhalers during regular daily activities, such as sports, school, day care, or traveling. Use of an optional wrist strap or clip allows the case to be carried in a variety of circumstances and allows the user to have an inhaler available at all times. An area for placement of prescription labels on the carrying case is also provided.

Similarly, the manual counting mechanism is simple to use and is easily understood by users of all ages and levels of education. The hasp or locking mechanism is easily opened and closed, yet creates a secure, water-resistant closure when locked.

The preferred embodiment depicted in the drawings is of one style of carrying case and counting mechanism. As new products come onto the market, it is anticipated that other sizes and styles of cases will be developed to accommodate these products. A three-digit manual counting mechanism is also depicted. The type of counting mechanism (mechanical, electrical, solar or other way of tallying the doses used that is currently not available) may be substituted for the present counting mechanism.

The preferred embodiment portrays placement of the counting mechanism inside the lid of the carrying case. This invention is clearly distinguished from prior art designs in that the present invention places the counting mechanism in or on the carrying case, whereas the prior art devices incorporate a counting mechanism into the plastic body of the inhaler. The present invention is designed to hold several styles and brands of inhalers and is much more economical than redesigning each inhaler body to accommodate a counting mechanism.

The number of inhaler users continues to rise. Because these inhalation devices are costly and subject to breakage, the carrying case will help decrease costs of inhalation therapy by preventing damage of the inhaler. The counting mechanism will help decrease costs by avoiding emergency refills and/or visits to emergency rooms due to empty inhaler canisters.

The present invention will be a valuable companion product for all individuals involved in the care of patients who use oral and nasal inhalers. As more new inhalation devices are introduced into the marketplace, the need for this product will increase as well. Thus the scope of the invention should be determined by the claims and future applications, rather than by the specific examples given.

Based on the information detailed in the specifications, objects and advantages of the present device, one skilled in the art can see that the present invention provides a highly-reliable, light-weight, water-resistant and economical way of protecting inhalation devices, as well as a way of tracking the number of doses administered from the device. The simplicity of design and operation allow use by individuals of all ages and education levels.

What is claimed is:

1. A case for carrying a medication dispenser which discretely meters a total number of fluid medication doses, wherein said carrying case comprises:

(a) a lower portion having rectangular, first and second side-walls connected to first and second end walls, and a bottom wall connected to said end walls and said side walls, wherein said walls form an oblong cavity for receiving the medication dispenser;

(b) a lid mounted by a hinge to said first end wall, wherein said lid is rotatable about said hinge to cooperate with said lower part forming a closed volume;

(c) a hasp attached to a second end wall of said lower portion, wherein said hasp engages an outer surface of said lid when said lid is rotated to cooperate with said lower portion; and (d) a counting mechanism embedded inside said lid so that said counting mechanism is only accessible from an underside of said lid, said counting mechanism for recording the number of dosages metered by the dispenser, whereby said counting mechanism notifies a user of an approximate number of remaining dosages in the dispenser.

2. The carrying case of claim 1, wherein said counting mechanism comprises a plurality of independently operated switch assemblies, said switch assemblies having numbered wheels actuated by a plurality of actuator buttons.

3. The carrying case of claim 1, wherein said lid and said lower portion reconstructed of a molded plastic material.

4. The carrying case of claim 1, further comprising a sealing means disposed between said lid and said lower portion for sealing said cavity when said hasp engages said lid.

5. A case for carrying a medication dispenser which discretely meters a total number of fluid medication doses, wherein said carrying case comprises:

(a) a main portion having a cavity for receiving the medication dispenser;

(b) a cover mounted by a hinge to said lower part such that said cover is rotatable about said hinge to cooperate with said main part;

(c) a latching mechanism attached to an outer surface of said case for securing said cover to said main portion; and (d) a counting mechanism embedded inside said lid so that said counting mechanism is only accessible from an underside of said lid, said counting mechanism for recording the number of dosages metered by the dispenser, whereby said counting mechanism notifies a user of an approximate number of remaining dosages in the dispenser.

6. The carrying case of claim 5, wherein said counting mechanism comprises a plurality of independently operated switch assemblies, said switch assemblies having numbered wheels actuated by a plurality of actuator buttons.

7. The carrying case of claim 6, wherein said counting mechanism is embedded in a polyurethane foam material.

8. The carrying case of claim 5, further comprising an O-ring surrounding a top opening of said main portion of said case, wherein said O-ring is engaged by a lower margin of said cover to form a sealed volume.

9. The carrying case of claim 5, wherein said cover and said main portion are constructed of a molded plastic material.

10. The carrying case of claim 9, further comprising a molded plastic eyelet attached to an outer surface of a top wall of said cover for receiving a means for securing said case to a user of the medication dispenser.

11. The carrying case of claim 5, wherein an upper rim of said main portion is sloped with respect to a bottom wall of said main portion to facilitate access to the dispenser.

12. A combination metered fluid medication dispensing apparatus and a case for carrying said dispensing apparatus, wherein said dispenser discretely meters a total number of fluid medication doses, said carrying case comprising:

(a) a lower portion having rectangular, first and second side-walls connected to first and second end walls, and a bottom wall connected to said end walls and said side walls, wherein said walls form an oblong cavity for receiving the medication dispenser;

(b) a lid mounted by a hinge to said first end wall, wherein said lid is rotatable about said hinge to cooperate with said lower part forming a closed volume;

(c) a hasp attached to a second end wall of said lower portion, wherein said hasp engages an outer surface of said lid when said lid is rotated to cooperate with said lower portion; and (d) a counting mechanism embedded inside said lid so that said counting mechanism is only accessible from an underside of said lid, said counting mechanism for recording the number of dosages metered by the dispenser, whereby said counting mechanism notifies a user of an approximate number of remaining dosages in the dispenser.

* * * * *